United States Patent [19]

Parker

[11] Patent Number: 4,797,260

[45] Date of Patent: Jan. 10, 1989

[54] ANTIBODY TESTING SYSTEM

[75] Inventor: James E. Parker, Long Beach, Calif.

[73] Assignee: V-Tech, Inc., Pomona, Calif.

[21] Appl. No.: 6,874

[22] Filed: Jan. 27, 1987

[51] Int. Cl.⁴ .................. B01D 29/00; B01L 11/00
[52] U.S. Cl. ............................ 422/101; 210/416.1; 436/807
[58] Field of Search ............ 422/69, 100, 101, 56–58; 436/807; 210/406, 416.1

[56] References Cited

U.S. PATENT DOCUMENTS

| 3,512,940 | 5/1970 | Shapiro | 422/101 |
| 3,628,915 | 12/1971 | Robertson | 422/69 |
| 4,166,102 | 8/1979 | Johnson | 436/807 |
| 4,180,383 | 12/1979 | Johnson | 422/69 |
| 4,624,929 | 11/1986 | Ullman | 422/100 |
| 4,632,901 | 12/1986 | Valkirs et al. | 436/807 |

FOREIGN PATENT DOCUMENTS 0141547  5/1985  European Pat. Off. ............ 422/69

Primary Examiner—Barry S. Richman
Assistant Examiner—Timothy M. McMahon
Attorney, Agent, or Firm—Drucker & Sommers

[57] ABSTRACT

A compound is bound to a membrane which is reactive to a component in a fluid sample which is being tested. Under the membrane a porous support is added. The fluid sample suspected of containing a specific component is drawn over the membrane and into the porous support by a piston and cylinder arrangement.

16 Claims, 2 Drawing Sheets

U.S. Patent   Jan. 10, 1989   Sheet 1 of 2   4,797,260
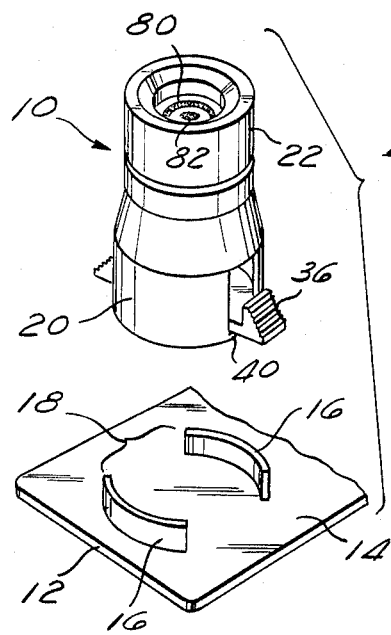
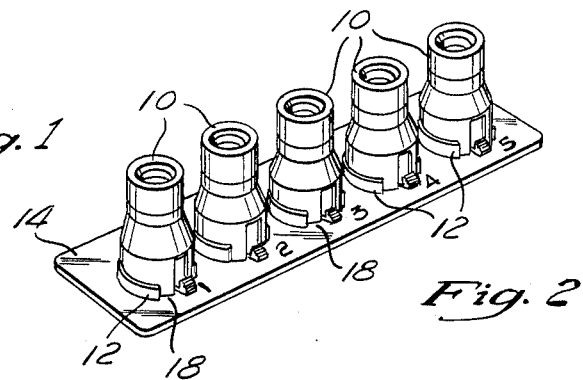
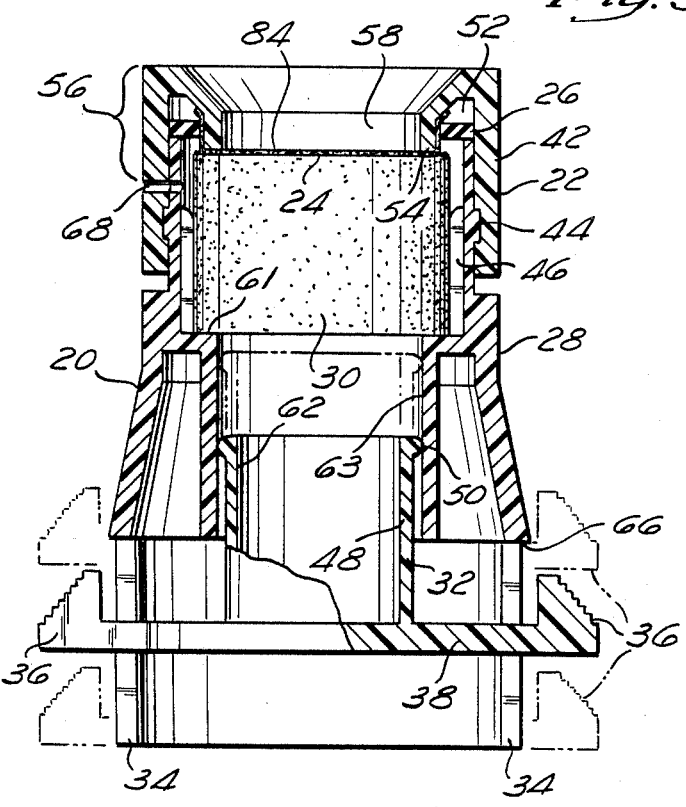
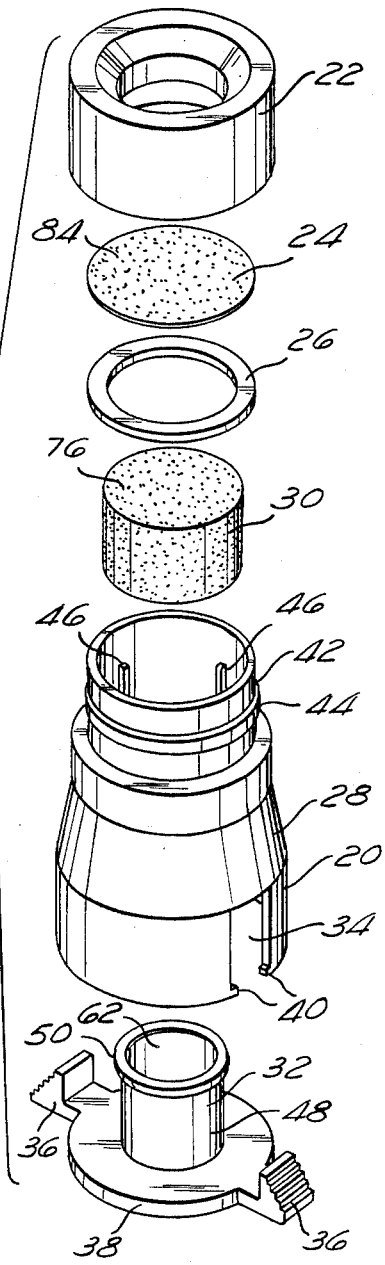
Fig. 1
Fig. 2
Fig. 3
Fig. 4

ANTIBODY TESTING SYSTEM

BACKGROUND OF THE INVENTION

1. Field of the Invention

This invention relates to apparatus and methods for testing for the presence of antigens using antibodies.

2. Prior Art

There are a variety of apparatuses designed to ease immuno testing.

One of these is U.S. Pat. No. 4,090,850 issued Chan. In this disclosure, antibody coated cellulose paper is used in radioimmunoassays in conjunction with the test apparatus comprising a receptacle tray with multiple wells, each of said wells having at its bottom an orifice such that the multiple wells can be simultaneously evacuated by a single source of reduced pressure.

In U.S. Pat. No. 3,888,629 issued Bagshawe, a reaction cell for the performance of radioimmunoassay determinations and the like is disclosed. Here two halves of the cell are joined together, separated by a membrane containing the necessary antibodies to form a particulate reaction product. The liquid reagents flow through the membrane under the influence of gravity.

U.S. Pat. No. 4,424,279 issued to Bohn discloses an immunoassay apparatus having a cylindrical tube that has a plunger filter assembly slideably fitted therein. The filter is dome shaped and contains beads sensitized with immunologically reactive material.

Greenspan U.S. Pat. No. 4,189,385 discloses a method and apparatus for separating serum or plasma from the formed elements of blood. The apparatus disclosed is generally similar to that of Bohn, except instead of a filter, a one way valve is disclosed.

In Buono U.S. Pat. No. 4,057,499, another apparatus for the separation of blood is taught. The apparatus is similar to the apparatus disclosed in Bohn and Greenspan. The one way valve of Greenspan is a filter, but unlike the filter in Bohn, it contains no immunologically reactive material.

Moore et al. U.S. Pat. No. 3,870,639 teaches yet another similar blood plasma separation device. Other filtration devices include U.S. Pat. No. 4,522,713 to Nussbaumer and U.S. Pat. No. 3,687,246 to Spinosa.

Bohn, Greenspan, and Buono rely on a slight pressure differential being created when a plunger portion is forced into contact with fluid contained in an outer tube. The fluid beneath the plunger filter or valve is then forced upwardly into a receiver tube fitted within the outer tube.

A problem with prior testing devices is that an analytical laboratory, complete with vacuum lines is required to use the devices. It would be advantageous to have a device that requires no external source of vacuum. The present invention provides an externally manipulable piston for creating a region of reduced air pressure beneath a membrane binding an analytic compound, preferably an antibody. The region of reduced pressure causes the fluid to be tested to be rapidly drawn through the membrane.

The entire surface of the membrane must be contacted by the fluid, and pool formation must be avoided. In a preferred embodiment, the present invention avoids this problem by the use of a filter member for membrane support that has a slightly convex membrane support surface.

SUMMARY OF THE INVENTION

An aspect of this invention is an apparatus for testing the presence of a specific compound in a fluid comprising:
- a membrane binding a component reactive with said compound;
- a body member having:
  - a piston housing; and
  - a membrane support adjacent to and contacting said membrane in vacuum communication with said piston housing;
- a piston, sealingly engaged for movement within said piston housing; and
- means for externally manipulating said piston to create a region of reduced air pressure when said piston is manipulated in a given direction.

A further aspect of this invention is an apparatus for the testing of the presence of an antigen in a fluid comprising:
- a porous filter member having a surface;
- a membrane binding at least one antibody reactive with said antigen, in intimate contact with said filter member;
- a body member having:
  - a piston housing; and
  - a support for the porous filter member in vacuum communication with said piston housing;
- a piston, sealingly engaged for movement within said piston housing; and
- a cap mated to said body securing said membrane across said surface of said filter member, having upward extension beyond the level of said surface, forming a depression for receiving a volume of said fluid to be tested, with the membrane as the bottom of the depression.

A further aspect of this invention is an apparatus for testing a fluid for the presence comprising:
- a membrane binding an antibody to said antigen;
- fluid removal means having a membrane side and a second side, said means removing fluid by adsoption; and
- air pressure reduction means on said second side.

A further aspect of this invention is an apparatus for analyzing a fluid for the presence of a specific compound by contacting the fluid with a membrane, retained within a first housing, having a component reactive for said compound, the improvement which comprises:
- a piston housing within said first housing, in fluid communication with said membrane, mounted immediately below said membrane; and
- a piston sealingly engaged for movement within said piston housing, said piston causing a region of reduced air pressure within said piston housing when moved in a given direction, causing fluid in contact with said membrane to be drawn through said membrane, to facilitate rapid contact of the fluid to be tested with the membrane.

BRIEF DESCRIPTION OF THE DRAWINGS

FIG. 1 is perspective view an embodiment of this invention, together with a preferred mounting means.

FIG. 2 is a perspective view of a plurality of mounted testing units.

FIG. 3 is an exploded perspective view of an embodiment of this invention.

FIG. 4 is sectional view of an embodiment of this invention.

DETAILED DESCRIPTION OF THE INVENTION

Figure 5:
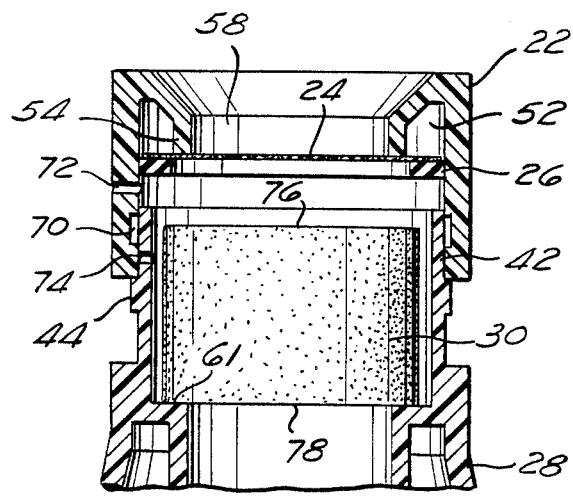
FIG. 5 is a sectional view of the embodiment of FIG. 2 prior to snap fitting the cap to the body member.

Referring to FIG. 1, the assembled antibody testing unit 10 can be placed onto a mounting means 12. A surface plate 14 has retaining walls 16 that have a handle relief 18 that allows the piston handle to be depressed to the surface plate. The fit of the retaining walls with the base of the unit 20 should be snug enough so that the unit does not wobble when used.

Referring to FIG. 2, a plurality of assembled testing units 10 are received by a plurality of mounting means. Then a series of tests can be run simultaneously. The series can be either several different tests for one individual or the same test for several individuals.

Referring to FIG. 3, a cap 22 receives membrane 24 containing a component reactive for the specific compound being tested for and a membrane retaining ring 26. Both the cap and the retaining ring are preferably made of molded plastic, although other materials known in the art will work as well. The membrane is made of material known to bind the components. It is preferred that the component be an antibody and the material bind proteins. Examples of such material include: nitrocellulose; Pall biodyne, which is a chemically activated nylon; and the like. The membrane retaining ring is of a dimension to snugly fit within the cap and not move once it is positioned in the cap.

A body member 28 receives porous filter member 30. The porous filter member is made of hydrophilic material. The body member is preferably made of the same material as the cap, preferably molded plastic. The body member has a base member 20 that extends upwardly and slopes inwardly. The base member terminates and a body extension 42 extends upwardly. A snap fit ring 44 encircles the body extension. Porous filter retaining members 46 disposed inside the body extension secure and center the porous filter member.

A piston member 32 is disposed in the body member below the porous filter member 30. Piston walls 48 extend upwardly from the piston base plate 38, and terminate in a periferal lip 50 that sealingly engages the piston housing when assembled. The sides of the body member contain two oppositely disposed slots 34 disposed in the base of the body member 20 to receive piston handles 36 that extend from the piston base plate and allow longitudinal movement of the piston handles. At the base of the slot is a handle retaining extension 40 to prevent the piston from accidentally disengaging from the body member when the piston is fully depressed.

The cap 22, including the membrane 24 and the retaining ring 26, is snap fit to the body member 28 which includes the porous filter member 30 and the piston 32. This assembly forms the final immunoassay unit 10. The cap, when snap fit to the body, will preferably be rotatable.

Referring now to FIG. 4, the cap member 22 is mated to the body member 28 by engaging the snap fit ring 44, which encircles the body extension 42. The ring is disposed within a snap fit relief, which encircles the cap.

A relief 52 in the cap member 28 receives the retaining ring. The membrane 24 is securely positioned within the relief between the retaining ring and the cap. A membrane engagement lip 54 on the cap forces the membrane into intimate contact with the entire surface of the porous filter member 30. The membrane retaining ring rests on the body extension 42, which forces the membrane retaining ring as far into the cap relief as possible. The membrane is secured in the cap relief by the membrane retaining ring and snugly covers the tap surface of the porous filter member.

It is important that the membrane be in intimate contact with the porous filter member for the porous filter member to draw fluid through the membrane by adsorption. An upward extension of the cap 56 allows a depression 58 to be formed for receiving the fluid to be tested. A volume of fluid to be tested can be placed in the depression. At the bottom of the depression is the top of the membrane 24. The top of the membrane has been impregnated with an antibody. This antibody will react with the antigen being tested for.

The porous filter member 30 is supported on an internal support 61. The porous filter member is disposed above a piston housing 63 and is in vacuum communication with the piston housing. That is, if the piston is depressed, creating a zone of reduced air pressure acts directly on the bottom surface of the porous filter. Within the piston housing, the piston member 32 is sealingly engaged with the walls of the piston housing by a sealing means. Preferably, the top of the circumferential wall terminates in a peripheral lip 50 extending outwardly, which engages the walls of the piston housing as the sealing means. In a preferred embodiment the piston has a piston wall 48 forming a central well 62. The central well can accumulate liquid reagents or washing fluids used during the test for the antigen. Piston handles 36 attached to the piston base plate 38 extend through a slot 34 allowing manipulation of the piston. The piston handles are oppositely disposed on the piston base plate. The piston is shown depressed about half way, but the piston can be depressed all the way to the bottom of the body member 28 and can be raised to the piston handle stop 66 as shown in phantom.

When the piston handles 36 are externally manipulated, usually by a lab technician, but possibly by automatic means, the piston moves downwardly to the lower position forming a region of reduced air pressure. Then, the fluid to be tested is rapidly drawn through the membrane.

In a preferred embodiment, the cap 22 and the body member 28 have vacuum release aperture 68 that extends from the exterior of the cap member through the body member to the atmosphere. The user of the unit can create an area of low pressure by rotating the cap thereby disaligning the hole in the cap and the hole in the body member. Alternatively, the user can leave the holes aligned, thereby preventing the piston from creating a low pressure region.

The porous filter member is a fluid removing means that intimately contacts the membrane. Fluid is drawn through the membrane, by the fluid removing means. The piston can act as an air pressure reduction means to rapidly draw fluid through the fluid removing means. The liquid reagents and washing fluids can be removed from contact with the membrane by the fluid removing means. If the fluid removing means is prevented from removing fluid, perhaps because it is saturated, the air pressure reduction means can draw excess fluid from the fluid removing means. The air pressure reduction means is in vacuume communication with the fluid removing means. The air pressure reduction means speeds tests conducted in the apparatus because there is no waiting for fluids filling the depression 58 or saturating the fluid removing means to drain by gravity.

Referring to FIG. 5, the cap 22 is shown as it would be in relation to the body 28 immediately before downward pressure is applied to snap fit the cap and body member. The membrane 24 is retained in the cap by the retaining ring 26, which is held into place by friction.

A snap fit relief 70 can receive the snap fit ring 44 when downward pressure is applied. Both the cap and the body must be made of resilient material, preferably molded plastic, to prevent breakage of either piece in this operation. The vacuum release aperature in the cap 72 will align with the vacuum release aperature 74 in the body member 28.

The porous filter member 30 has a flat top surface 76 and a flat bottom surface 78. The porous filter member is retained by the internal support 61. The porous filter is disposed above the piston housing 63. When the cap is snap fit onto the body member, the body member extension 42 engages the retaining ring 26 and forces it into the relief 52 in the cap 22, thereby deforming the membrane and stretching it tightly across the top surface of the porous filter member. The membrane engagement lip forces the membrane downwardly into the porous filter member creating a relief along the circumference of the top surface of the porous filter member. In this way, intimate contact of the entire surface of the membrane with the top surface of the porous filter member is assured, that is, the membrane covers and contacts all points of the top of the porous filter member. It is preferred that the top surface of the porous filter member be flat, but since the filter material can be easily deformed, a slightly convex top surface is preferrably employed. It is critical that there are no concavities in the depression once the unit is assembled, where fluids might pool. The pressure of the snap fit will also slightly deform the bottom circumference of the porous filter member that sits on the internal support.

It is preferred that the body member, the cap and the piston all be made of moldable plastic. Such construction provides low cost components that are easily assembled. The outward extension of the piston wall has superior wall engagement properties when made of molded plastic. The porous filter member can be made of any hydrophillic adsorbant, for example, filter paper.

Figure 6:
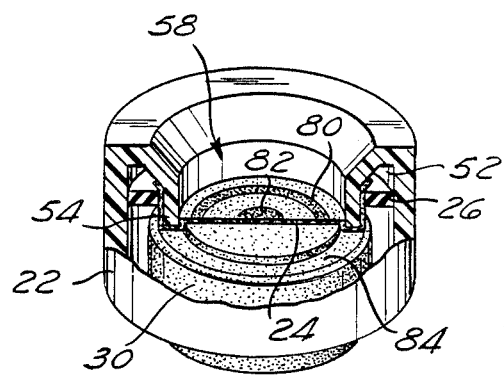
FIG. 6 is a partially cut away perspective view of the cap of this invention.

Referring to FIG. 6 the membrane 24 is forced into contact with the porous filter 30 by the membrane engagement lip 54. This deforms the porous filter forming a circular depression 84. The edge of the membrane is retained by the retaining ring 26 in the relief 52 in the cap 22. The top surface of the membrane forms the bottom of the depression 58. The antibodies used in the test impregnate the top surface of the membrane. If two antibodies are used they can form a pattern, in the case shown, a ring 80 and a central dot 82. It will be appreciated that normally the unreacted pattern is invisible, and that only a positive test results in the entire pattern being visible.

As shown, the retaining ring is forced as deeply into the recess 52 as possible, and is kept there by the body member extension. The body is not shown in this drawing, but the cap having the deformed porous filter is snap fitted to the body.

In use, the unit is mounted on a mounting means. The membrane will have been impregnated with an antibody to an antigen that is to be test for. For example, in a pregnancy test, the membrane will have been impregnated with anti-hCG. The fluid containing the antigen can be either a urine sample or a blood serum sample. After the fluid has been contacted with the membrane and withdrawn into porous filter member, a second labeled antibody is contacted with the membrane. If the antigen is present, it will be bound to the first antibody on the surface of the membrane. The antigen will then bind the second labeled antibody. This is sometimes referred to in the art as a "forward sandwich" assay. See for example, U.S. Pat. No. 4,376,110 issued David et al. If the antigen is present, then the label will be present on the surface of the membrane. The label can be a radiometric, a fluormetric label, and enzymatic label, a colorometric label, or any of a number of other labels well known in the art.

One advantage of the device of the present invention is that tests can be run on a wide variety of compounds in fluids. For example, if the pH of water is to be tested in the device of the present invention, the membrane could be litmus paper. Other similar non-antibody tests will immediately suggest themselves to the skilled artisan. Of course, the preferred tests are antibody tests. The device of the present invention can facilitate tests for a wide range of antigens. A great advantage of the device is that different fluids can be tested for. For example, blood serum and urine can both be tested in the same unit.

Of course, almost any antigen can be analyzed for using the apparatus of the present invention. For example, one can test for hGC, for viral infections such as AIDS, drugs such as cocaine or heroin, difficult to diagnose bacterial diseases such as chlamydia, and other antigens.

In a preferred embodiment, at least two different antibodies are present on the membrane, for example, anti-LCG and anti-horseradish peroxidase. The first antibody tests for the presence of the antigen. The second can test if the reagents are working properly, that is, it should always be a positive test if the reagents are added in the correct order. When colorometric labels are used, the two antibodies can be placed on the membrane to form a pattern. For example, a minus if the test is negative, or a plus if the test is positive, or a ring and an inner dot forming a bullseye if the test is positive, and a ring if the test is negative. The membrane is impregnated using the apparatus of our copending application Ser. No. 032,460 .

The embodiments described are the currently preferred embodiments, but the scope of the invention should not be considered limited by anything other than the appended claims.

I claim:

1. An apparatus for testing, comprising:
    a membrane having a component reactive with a specific compound bound to the membrane, said membrane allowing the passage of liquid;
    a body member having:
    an internal piston housing; and
    a porous membrane support mounted adjacent said piston housing having a first side adjacent to and contacting said membrane and a second side defining the upper surface of said piston housing; and
    a piston, sealingly engaged with said piston housing for movement from a first position to a second position within said piston housing to create a zone of reduced pressure below said porous membrane support to facilitate passage of liquid through said porous membrane support.

2. The apparatus of claim 1 further comprising means for externally manipulating said piston said means comprises a pair of oppositely disposed piston handles, extending through the body member.

3. The apparatus of claim 1 wherein the piston is molded plastic.

4. The apparatus of claim 1 wherein said membrane support is a filter member having a support surface supported within said body member.

5. The apparatus of claim 4 wherein said member is in intimate contact with said support surface.

6. The apparatus of claim 5 wherein said means comprises a cap mated to said body member, having an upward extension beyond the surface of said filter member, forming a depression for receiving a volume of the fluid to be tested, with the membrane forming the bottom of said depression.

7. The apparatus of claim 5 wherein said support surface is slightly convex.

8. The apparatus of claim 5 further comprising specific compound is an antigen and said component reactive with the specific compound is an antibody.

9. The apparatus of claim 8 wherein the antibody is anti-hCG.

10. An apparatus for testing comprising:
a porous member having a first surface and a second surface;
a membrane having at least one antibody bound to the membrane, and positioned in intimate contact with the first surface of said porous member;
a body member having:
an internal piston housing;
a means for mounting the porous member within the body member, the second surface of said porous member defining the upper surface of said piston housing;
a piston sealingly engaged for movement from a first position to a second position within said piston housing to create a zone of reduced pressure below said porous member to facilitate the passage of liquid through the porous member;
a cap mated to said body securing said membrane across said first surface of said porous member, having an upward extension beyond the level of said first surface forming a depression for receiving a volume of a fluid suspected of containing an antigen reactive with said antibody with the membrane forming the bottom of the depression.

11. The apparatus of claim 10 wherein said cap is mated by snap fit to said body.

12. The apparatus of claim 10 wherein said membrane has at least two antibodies bound thereto, a first for testing the viability of the reagents and a second for reacting with an antigen.

13. The apparatus of claim 10 wherein said body member is substantially cylindrical.

14. The apparatus of claim 10 wherein the piston has a molded base plate having handles extending outwardly therefrom, and a centrally positioned circumferal wall extending upwardly, terminating in a peripheral lip extending outwardly.

15. The apparatus of claim 10 wherein said body has two slots disposed on opposite sides of said body, and said piston having two handles, extending through the slots.

16. The apparatus of claim 15 wherein said slots have means for retaining said handles when said handles are depressed to the bottom of said body member.

* * * * *